United States Patent
Hoshino et al.

(10) Patent No.: US 9,629,600 B2
(45) Date of Patent: *Apr. 25, 2017

(54) MEDICAL IMAGING SYSTEM

(71) Applicant: Konica Minolta, Inc., Chiyoda-ku, Tokyo (JP)

(72) Inventors: Yoshihide Hoshino, Hachioji (JP); Junko Kiyohara, Hino (JP); Atsushi Takahashi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 142 days.

This patent is subject to a terminal disclaimer.

(21) Appl. No.: 14/551,119

(22) Filed: Nov. 24, 2014

(65) Prior Publication Data

US 2015/0150529 A1    Jun. 4, 2015

(30) Foreign Application Priority Data

Nov. 29, 2013    (JP) .................................. 2013-246853

(51) Int. Cl.
*G03H 5/00* (2006.01)
*A61B 6/00* (2006.01)
(Continued)

(52) U.S. Cl.
CPC .......... *A61B 6/5217* (2013.01); *A61B 6/4035* (2013.01); *A61B 6/484* (2013.01);
(Continued)

(58) Field of Classification Search
CPC ................. G03H 5/00; G21K 2207/00; G21K 2207/005; A61B 6/484; G01N 23/00; G01N 23/04; G01N 23/20075; G01B 15/02; G06T 7/00; G06T 7/0012; G06T 7/0079; G06T 7/0081; G06T 7/0083; G06T 7/0085; G06T 2207/30004; G06T 2207/30008

USPC ................................ 378/36, 54, 62; 382/128
See application file for complete search history.

(56) References Cited

U.S. PATENT DOCUMENTS

| 5,812,629 | A | 9/1998 | Clauser | |
|---|---|---|---|---|
| 9,107,638 | B2 * | 8/2015 | Hoshino | ................ A61B 6/484 |
| 2014/0169522 | A1 | 6/2014 | Hoshino | |

FOREIGN PATENT DOCUMENTS

| AU | 2007209792 A1 | 9/2007 |
|---|---|---|
| JP | 2008200359 A | 9/2008 |

(Continued)

OTHER PUBLICATIONS

Extended European Search Report corresponding to Application No. 14191556.1-1660; Date of Mailing: Mar. 31, 2015.

(Continued)

*Primary Examiner* — Jurie Yun
(74) *Attorney, Agent, or Firm* — Cantor Colburn LLP

(57) ABSTRACT

A medical imaging system includes an X-ray Talbot imaging apparatus and an image processing apparatus. The X-ray Talbot imaging apparatus includes a controller which generates reconstructed image(s) including at least a differential phase image from image signals of an imaged subject. The image processing apparatus measures the thickness of cartilage in the joint in the differential phase image or an image generated from the differential phase image, by reference to at least one of i) an edge of a bone in the joint identified in a reconstructed image or an image generated from the reconstructed image and ii) an edge of the cartilage identified in the differential phase image or the image generated from the differential phase image.

15 Claims, 10 Drawing Sheets

(51) Int. Cl.
*G06T 7/00* (2017.01)
*G06T 7/60* (2017.01)

(52) U.S. Cl.
CPC ............ *A61B 6/505* (2013.01); *G06T 7/0083* (2013.01); *G06T 7/602* (2013.01); *G06T 2207/10116* (2013.01); *G06T 2207/30008* (2013.01)

(56) References Cited

FOREIGN PATENT DOCUMENTS

| JP | 2014117485 A | 6/2014 |
| WO | 0132079 A2 | 5/2001 |
| WO | 0223483 A2 | 3/2002 |
| WO | 2004051301 A2 | 6/2004 |
| WO | 2011033798 A1 | 3/2011 |

OTHER PUBLICATIONS

Massimo Marenzana et al., "Visualization of Small Lesions in Rat Cartilage by Means of Laboratory-Based-X-Ray Phase Contrast Imaging," Physics in Medicine and Biology, Institute of Physics Publishing, Bristol, GB; Nov. 2012, pp. 8173-8184, vol. 57, No. 24.

Nagashima Masabumi et al. "Optimization of Joint and Cartilage: Diagnostic Potential of Differential Interferential Contrast X-Ray Imaging", Proceedings of the 14th Japanese Research Society of Clinical Anatomy, Sep. 11, 2010. Japanese Research Society of Clinical Anatomy, Feb. 2011, No. 11, pp. 56-57.

* cited by examiner

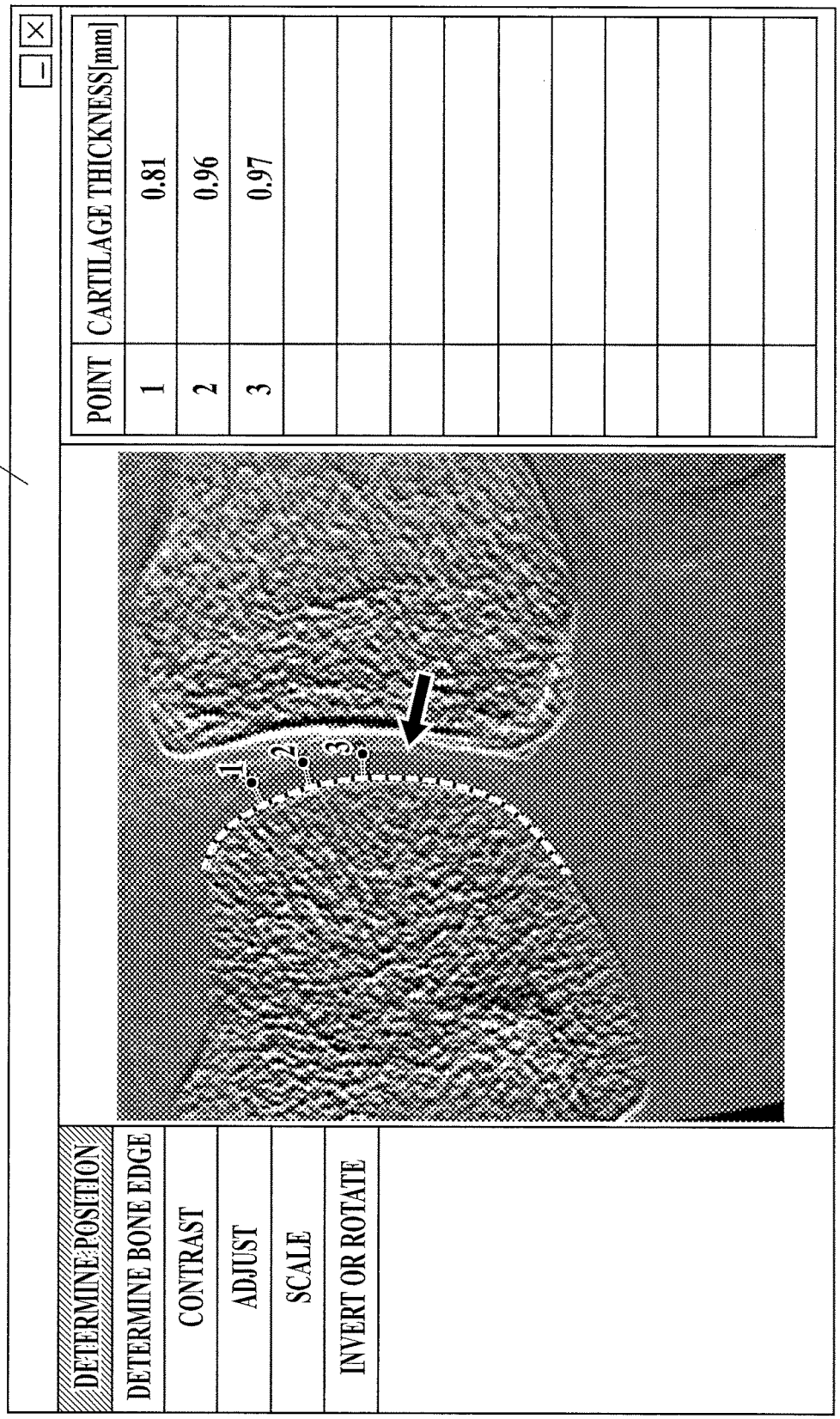

MEDICAL IMAGING SYSTEM

CROSS REFERENCE TO RELATED APPLICATIONS

The present invention claims priority under 35 U.S.C. §119 to Japanese Application No. 2013-246853 filed Nov. 29, 2013, the entire content of which is incorporated herein by reference.

BACKGROUND OF THE INVENTION

1. Field of the Invention

The present invention relates to a medical imaging system, particularly to a medical imaging system including an X-ray Talbot imaging apparatus.

2. Description of Related Art

In general, simple X-ray images (i.e., absorption images) of patient's joint cartilage cannot be captured with traditional silver halide films. Magnetic resonance imaging (MRI), which can image joint cartilage, produces low-definition images and cannot always measure quantitative feature values, such as the levels of defect, damage, and abrasion of cartilage due to arthritis or arthrorheumatism. In a conventional diagnosis of knee arthrorheumatism, a doctor estimates the thickness, abrasion or the like of the cartilage that is not visualized in a simple X-ray image of patient's knee, from the distance of a gap in the knee joint.

An X-ray imaging apparatus is known that includes a Talbot interferometer by the Talbot effect, which achieves imaging by sensing the phase shifts in X-rays passing through an object. An X-ray imaging apparatus is also known that includes a Talbot-Lau interferometer which is an application of the Talbot interferometer (see U.S. Pat. No. 5,812,629, Japanese Unexamined Patent Application Publication No. 2008-200359, and WO2011/033798, for example). In this specification, an X-ray imaging apparatus including a Talbot interferometer or a Talbot-Lau interferometer is called "X-ray Talbot imaging apparatus". In specific, an X-ray Talbot imaging apparatus may be not only an X-ray imaging apparatus including a Talbot interferometer but also an X-ray imaging apparatus including a Talbot-Lau interferometer.

An X-ray Talbot imaging apparatus produces one or more moire images, which can be reconstructed into at least three types of images by analyzing multiple moire images taken by a scheme using the principle of fringe scanning or by analyzing a single moire image by the Fourier transform. The three types of images consist of an absorption image (the same as an X-ray absorption image explained above) reflecting the contrast produced by X-ray absorption, a differential phase image reflecting the contrast based on phase information, and a small-angle scattering image reflecting the contrast produced by small-angle scattering.

The inventors have applied an X-ray Talbot imaging apparatus to imaging of joint cartilage and found that an X-ray Talbot imaging apparatus can produce at least differential phase images of joint cartilage in an incised joint, as disclosed in Nagashima Masabumi and seven others. "Optimization of Joint and Cartilage: Diagnostic Potential of Differential Interferential Contrast X-ray Imaging". Proceedings of the 14th Japanese Research Society of Clinical Anatomy, Sep. 11, 2010. Japanese Research Society of Clinical Anatomy, February 2011, No. 11, pp. 56-57, http://www.jrsca.jp/contents/records/ (accessed on Nov. 21, 2013). The inventors have also found that reconstructing a captured moire image of a joint in a living body instead of an incised joint the image also produces at least a differential phase image of joint cartilage.

With a conventional X-ray imaging apparatus, which cannot visualize cartilage in a captured image of patient's joint as described above, the doctor should estimate the thickness, abrasion or the like of the cartilage from the distance of a gap between two bones forming, for example, a knee joint. Consequently, the thickness or the like of cartilage cannot be quantitatively measured. Since the estimation depends on the experience or techniques of the radiologist, the estimated thickness or the like of cartilage may vary depending on the radiologist, inhibiting the consistency of the estimations.

If patient's joint cartilage is visualized in a differential phase image reconstructed from moire images taken with an X-ray Talbot imaging apparatus, the thickness or the like of the cartilage can be quantitatively measured in reference to the image of the cartilage. Referring to the differential phase image of the cartilage, the thickness or the like of the cartilage can be consistently measured independently of the experience or techniques of the radiologist. Thus, a measure is required which allows a medical imaging system including an X-ray Talbot imaging apparatus to quantitatively and consistently measure the thickness or the like of patient's joint cartilage from a differential phase image reconstructed from moire images taken with the X-ray Talbot imaging apparatus.

SUMMARY OF THE INVENTION

An object of the present invention, which has been made to solve the above problems, is to provide a medical imaging system that quantitatively and consistently measures the thickness or the like of cartilage from the joint cartilage visualized in a differential phase image reconstructed from moire images taken with an X-ray Talbot imaging apparatus.

In order to solve the problems set forth above, according to an aspect of a preferred embodiment of the present invention, there is provided a medical imaging system including: an X-ray Talbot imaging apparatus including: an X-ray source which emits X-rays, an X-ray detector including conversion elements to generate an electrical signal according to the emitted X-rays, and reading the electrical signal generated by the conversion elements, as an image signal, a subject table to hold a subject for a joint of the subject to be imaged, and a controller which generates a reconstructed image from the image signal of the imaged subject, the reconstructed image including at least a differential phase image; and an image processing apparatus which measures a thickness of cartilage in the joint in the differential phase image or an image generated from the differential phase image, by reference to at least one of i) an edge of a bone in the joint identified in the reconstructed image or an image generated from the reconstructed image and ii) an edge of the cartilage identified in the differential phase image or the image generated from the differential phase image.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 3 is an example image on a screen, showing a differential phase image of an edge of a bone in an identified joint and the thickness or the like of the cartilage at a specified point.

DESCRIPTION OF THE PREFERRED EMBODIMENTS

Embodiments of a medical imaging system of the present invention will now be described with reference to the attached drawings.

In this embodiment, an X-ray Talbot imaging apparatus 1 in a medical imaging system is a Talbot-Lau interferometer including a ray source grating (or multi grating or multi-slit grating) 12 described later. Alternatively, in the invention, the X-ray Talbot imaging apparatus 1 may be a Talbot interferometer including only a first grating (or G1 grating) 14 and a second grating (or G2 grating) 15 but no ray source grating 12.

[Configuration of Medical Imaging System]

Figure 1:
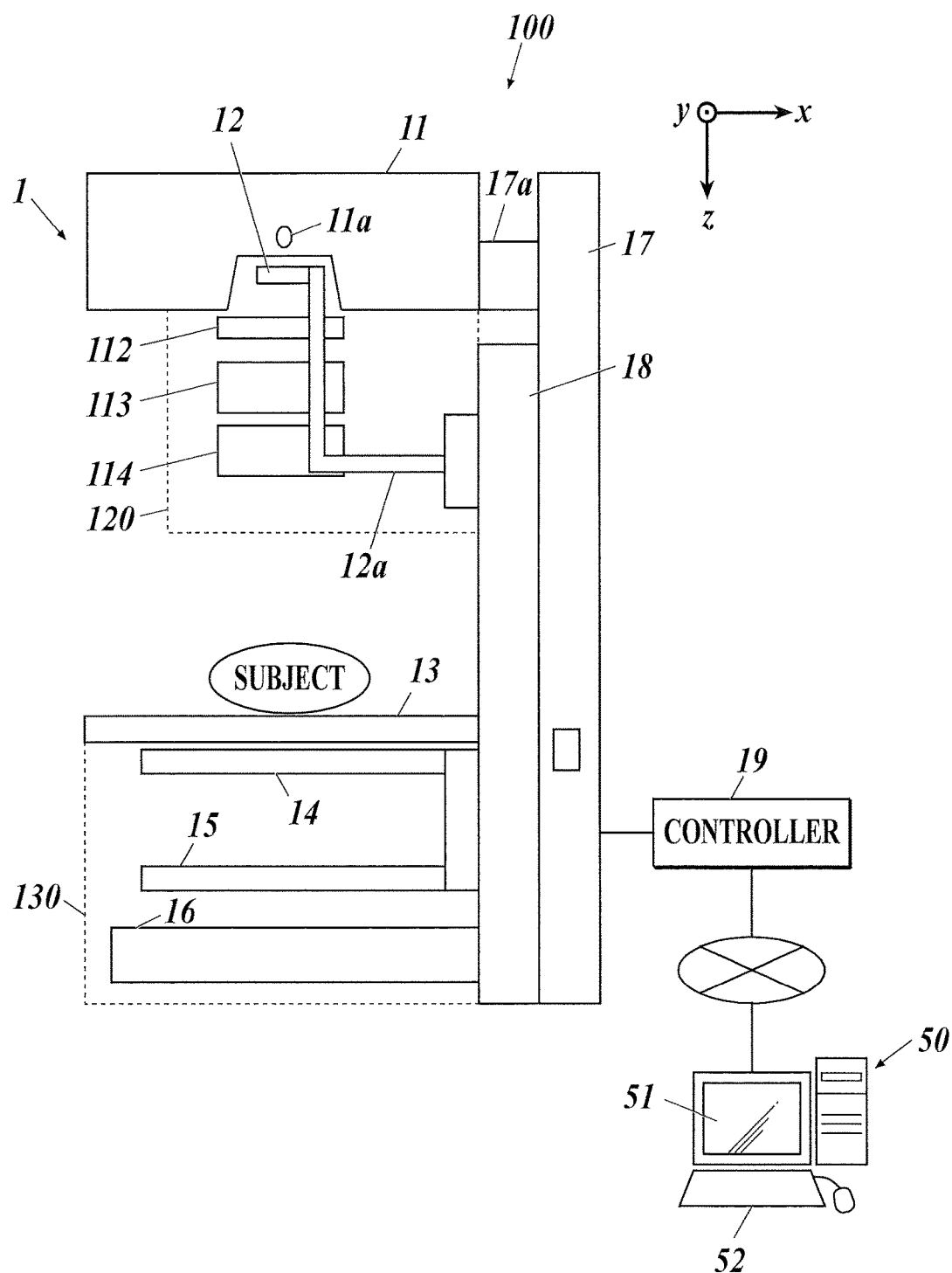
FIG. 1 is a schematic general view of a medical imaging system of an embodiment.

The configuration of the medical imaging system of this embodiment will now be described. FIG. 1 is a schematic general view of a medical imaging system 100 of this embodiment. In this embodiment, the medical imaging system 100 includes the X-ray Talbot imaging apparatus 1 and an image processing apparatus 50.

[Configuration of X-Ray Talbot Imaging Apparatus 1]

The X-ray Talbot imaging apparatus 1 includes a Talbot interferometer or Talbot-Lau interferometer as described above. The Talbot effect, which is the principle of a Talbot interferometer, refers to a phenomenon in which when coherent X-rays pass through the first grating (G1 grating) with slits at regular intervals, the image of the grating is formed at regular intervals along the direction of the propagating X-rays (see Japanese Unexamined Patent Application Publication No. 2008-200359, for example). The formed images are called self-images. The Talbot interferometer has a second grating (G2 grating) at a location of a self-image, and forms moire fringes. Positioning a subject at the paths of the X-rays disrupts the moire fringes. For this reason, the X-ray Talbot imaging apparatus 1 is configured to capture a moire image with moire fringes disrupted by the subject. The configuration of the X-ray Talbot imaging apparatus 1 of this embodiment will be described below.

In this embodiment, the X-ray Talbot imaging apparatus 1 includes a radiation generator 11, a ray source grating 12, a subject table 13, a first grating 14, a second grating 15, an X-ray detector 16, a support 17, a base 18, and a controller 19. In this embodiment, as illustrated in FIG. 1, the X-ray Talbot imaging apparatus 1 is configured to emit radiation toward the subject on the lower side from the radiation generator 11 on the upper side. Alternatively, in the invention, the radiation may be emitted in any direction, e.g., the horizontal direction.

The radiation generator 11 includes an X-ray source 11a which is, for example, a Coolidge X-ray source, a rotating anode X-ray source, or other sources commonly used in medical practice. In the state shown in FIG. 1, the ray source grating 12 is provided below the radiation generator 11. In this embodiment, the ray source grating 12 is not mounted to the radiation generator 11 but to a fixer 12a on the base 18 on the support 17 to prevent vibrations of the radiation generator 11 generated by the rotation of the anode of the X-ray source 11a from propagating to the ray source grating 12. In this embodiment, to avoid or reduce the vibrations of the radiation generator 11 propagating to the support 17 or other components in the X-ray Talbot imaging apparatus 1, a cushion 17a is provided between the radiation generator 11 and the support 17.

In this embodiment, the ray source grating 12, the first grating 14, and the second grating 15 have multiple slits (not shown) at regular intervals in the y direction perpendicular to the z direction parallel to the irradiation direction. In this case, the slits extend in the x direction. The fixer 12a in this embodiment is mounted with the ray source grating 12, a filter (additional filter) 112 to modify the quality of the radiation passing through the ray source grating 12, an irradiation field diaphragm 113 to narrow the irradiation field, and an irradiation field lamp 114 to adjust the position before the irradiation by exposing a subject to visible light instead of radiation. Note that the ray source grating 12, the filter 112, and the irradiation field diaphragm 113 are not necessarily positioned in this order. In this embodiment, a first covering unit 120 is provided around the ray source grating 12 and other components to protect them.

A subject table 13 is provided between the radiation generator 11 and the first grating 14 to hold a subject (a joint of the patient) for radiography. In the state shown in FIG. 1, the first grating 14 and the second grating 15 are provided below the subject table 13, and the X-ray detector 16 is provided directly below the second grating 15. The X-ray detector 16 has an array of conversion elements (not shown) to generate an electrical signal according to emitted X-rays, and reads the electrical signal generated by the conversion elements, as an image signal, to capture a moire image on the second grating 15. A second covering unit 130 is provided around the first grating 14, the second grating 15, and the X-ray detector 16 to protect them from a leg or other parts of the patient. If the X-ray Talbot imaging apparatus 1 is configured to capture multiple moire images by fringe scanning, a transfer device (not shown) is provided therein to move any one of the ray source grating 12, the first grating 14, and the second grating 15, or both the first grating 14 and the second grating 15 in the y direction. Alternatively, in the invention, the X-ray Talbot imaging apparatus 1 may capture a single moire image without fringe scanning, and the controller 19 may analyze the moire image by Fourier transform to generate an absorption image or a differential phase image by reconstruction.

The controller 19 in this embodiment is a computer including a central processing unit (CPU), a read only memory (ROM), a random access memory (RAM), an input/output interface, and other components connected via a bus, which are not shown in the drawing. Alternatively, the controller 19 may be a dedicated controller. Although not shown in the drawing, the controller 19 includes any appropriate unit or device, such as an input unit or a display unit. The controller 19 comprehensively controls the X-ray Talbot imaging apparatus 1, for example, controls the tube voltage or irradiation time for the radiation generator 11. If the X-ray Talbot imaging apparatus 1 captures multiple moire images by fringe scanning as described above, the controller 19 can control the distance or speed of the movement of, for example, the first grating 14 caused by the transfer device and adjust the timings of the movement of the grating and the emission of radiation from the radiation generator 11.

Furthermore, the controller 19 can reconstruct an X-ray absorption image, a differential phase image, and a small-angle scattering image from one or more captured moire images. In this embodiment, the controller 19 reconstructs an X-ray absorption image, a differential phase image, a small-angle scattering image, and any other image produced by composition of these images, from image signals (i.e. moire image(s)) of the subject captured by the X-ray detector 16. The controller 19 reconstructs at least a differential phase image among these images.

A separate control unit (not shown) for controlling the radiation generator 11 may be provided in addition to the controller 19. The controller 19 and the image processing apparatus 50 are separated in this embodiment, but may be integrated into a single unit. The controller 19, the image processing apparatus 50, and the generator for the radiation generator 11 may be separated. Alternatively, two or more of these units may be integrated into a single unit.

[Configuration and Processing of Image Processing Apparatus 50]

In the medical imaging system 100 of this embodiment, as shown in FIG. 1, the controller 19 of the X-ray Talbot imaging apparatus 1 is connected to the image processing apparatus 50 via a network such as a local area network (LAN). The image processing apparatus 50 in this embodiment is a general-purpose computer like the controller 19 of the X-ray Talbot imaging apparatus 1, but may be a dedicated processor, instead. The image processing apparatus 50 in this embodiment includes a display 51 including a cathode ray tube (CRT) or liquid crystal display (LCD) and an input unit 52 composed of a keyboard, a mouse, and other units.

Figure 2A:
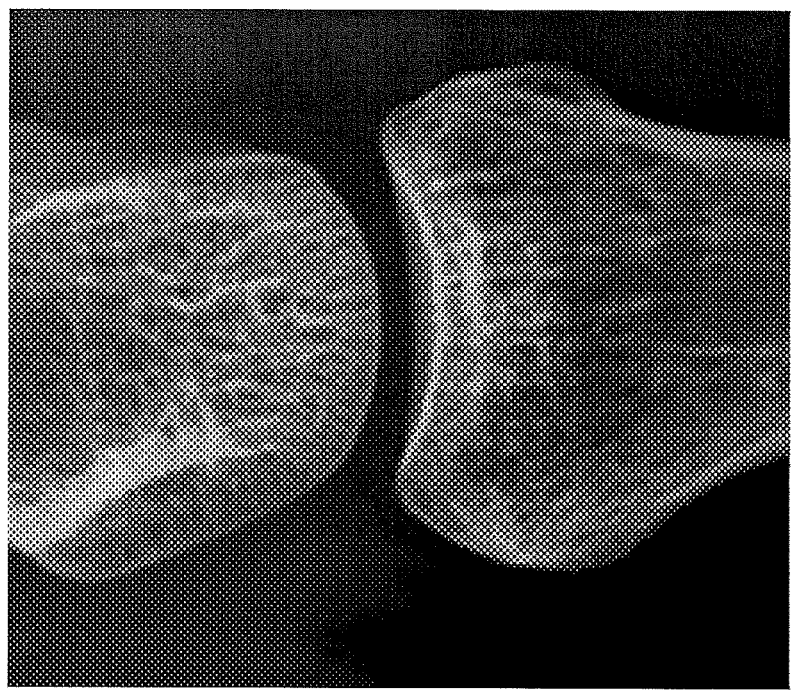
FIG. 2A is an example absorption image (photograph) of a joint.
Figure 2B:
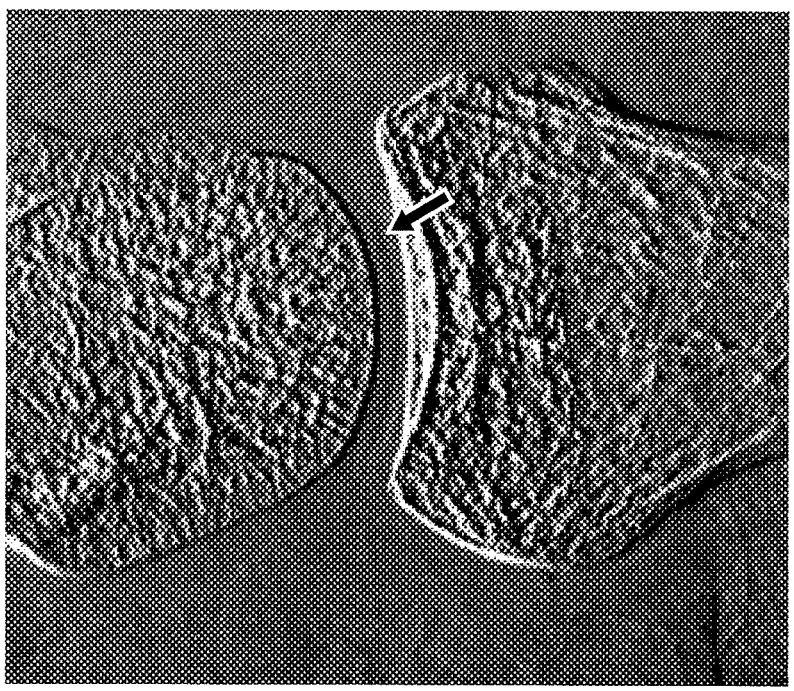
FIG. 2B is an example differential phase image (photograph) of a joint, showing an edge of joint cartilage.

For instance, the controller 19 of the X-ray Talbot imaging apparatus 1 reconstructs an absorption image in FIG. 2A, a differential phase image in FIG. 2B, or a small-angle scattering image (now shown) from a moire image of a finger joint of the patient (subject). Joint cartilage is difficult to visualize in an absorption image. The edge (surface) of joint cartilage (or simply cartilage edge), however, can be visualized in a differential phase image as indicated by the arrows in FIGS. 2B and 3.

The image processing apparatus 50 in this embodiment quantitatively measures the thickness or the like of the joint cartilage based on the position of the edge of a bone or joint cartilage in patient's (subject's) joint identified in a differential phase image created from any of the above-listed images: the absorption image, the differential phase image, and the small-angle scattering image. The configuration of such an image processing apparatus 50 will now be described with some examples. The medical imaging system 100 of this embodiment, which includes the image processing apparatus 50, will also be described in terms of its operation.

As described above, the controller 19 of the X-ray Talbot imaging apparatus 1 generates at least a differential phase image, but does not always generate an absorption image or a small-angle scattering image through reconstruction. Hence, the absorption image, the differential phase image, and the small-angle scattering image generated by the controller 19 of the X-ray the Talbot imaging apparatus 1 by reconstruction hereinafter are collectively called "reconstructed images". The reconstructed images also include images generated from absorption images, differential phase images, or small-angle scattering images in the controller 19 of the X-ray the Talbot imaging apparatus 1.

As described later, the image processing apparatus 50 in this embodiment may be configured to quantitatively measure the thickness R of joint cartilage from a differential phase image showing the joint cartilage or its edge. Alternatively, an additional image may be used which is generated by subtracting the pixel values of a differential absorption image (based on the absorption image generated from the moire image as described above) from the pixel values of the differential phase image. The joint cartilage appears more clearly than the bone in such an additional image, resulting in accurate measurement of the thickness R of the cartilage. Each pixel in the differential absorption image has a value calculated by multiplying a predetermined factor by a difference between the value of a corresponding pixel of the absorption image and the value of the adjacent pixel. The difference may be a difference between the values of the adjacent pixels, which serves as the value of these adjacent pixels, or calculated through a differentiation filter such as a Sobel filter.

The image processing apparatus 50 quantitatively measures the thickness R of the joint cartilage from a differential phase image in the explanation below. Alternatively, the image processing apparatus 50 may measure the thickness R of the cartilage from an image based on a differential phase image, such as the additional image described above.

[Exemplary Configuration 1]

The edge of a bone in a joint of the patient (subject) clearly appears in an absorption image (FIG. 2A), a differential phase image (FIG. 2B), and a small-angle scattering image (not shown). Hence, the position of the edge of the bone can be identified in any of these reconstructed images. In Exemplary Configuration 1, the image processing apparatus 50 first identifies the position of the edge of the bone from a reconstructed image.

For example, in the reconstructed absorption image in FIG. 2A, the pixel value (brightness) steeply decreases at the edge portion of the bone when a target pixel row is observed pixel by pixel from left to right. In the reconstructed differential phase image of FIG. 2B, the pixel value (brightness) steeply decreases at the edge portion of the bone when a target pixel row is observed pixel by pixel from left to right. In view of this, a predetermined threshold is set for the fluctuating range of pixel value, and each average pixel value is calculated while a target pixel row in such a reconstructed image is scanned pixel by pixel from left to right. Instead of the average pixel value, the moving average for 50 or 100 pixels may be calculated. If the absolute value of the difference between the value of a target pixel and the calculated average pixel value or moving average (in this case, the pixels based on which the moving average is calculated do not include the target pixel) exceeds the threshold, the target pixel is identified as the edge portion of the bone in the joint in the pixel row. The reconstructed image is sequentially scanned row by row for the same procedure described above to identify the edge portions of the bone in the joint in the reconstructed image.

An object of calculating such a difference (or its absolute value) between the value of the target pixel and the average pixel value or moving average for the pixels in the pixel row of the reconstructed image is to remove variations in entire brightness among images (including absorption images, differential phase images, and other reconstructed images). Instead of the threshold of the difference, the threshold of the value (quotient) obtained by dividing the difference by the average pixel value or moving average may be used. In this case, a pixel with a quotient (or its absolute value) exceeding the threshold is identified as the edge portion of the bone in the joint. Thus, the image processing apparatus 50 may identify the edge of the bone in any process. In specific, the edge of the bone in the joint may be manually identified by the user by observing a reconstructed image displayed on the display 51 of the image processing apparatus 50, instead of automatic identification by the image processing apparatus 50 as described above.

Even if the right-left direction of the finger is reversed in an absorption image (see FIG. 2A), the pixel value (brightness) is still high in the bone area and low in the adjacent area in the image. In contrast, if the right-left direction of the finger is reversed in a differential phase image (see FIG. 2B), the brightness is reversed at the edge of the bone in the joint. In particular, in a differential phase image in FIG. 2B, if the pixel value (brightness) is low at the edge of the bone at the left side of the image, the pixel value (brightness) is high at the edge of the bone at the right side of the image. When a bone having a convex face in the joint (having an articular head) is on the left of the differential phase image as shown in FIG. 2B, the pixel value steeply decreases at a pixel corresponding to the edge of the bone in the joint, when every pixel is sequentially observed pixel by pixel from left to right in a target pixel row in the differential phase image. Although not shown, in a differential phase image in which the bone having a convex face in the joint is on the right, the pixel value steeply increases at a pixel corresponding to the edge of the bone in the joint, when every pixel is sequentially observed pixel by pixel from right to left in a target pixel row in the differential phase image. The process in the image processing apparatus 50 for identifying the edge of the bone in the joint is therefore arranged in consideration of such individual properties of the reconstructed image.

The above process may identify not only the convex edge of the bone in the joint (i.e., the bone at the left side of the images of FIGS. 2A and 2B) but also the concave edge of the bone in the joint (i.e., the bone having an articular fossa at the right side of the images of FIGS. 2A and 2B). In such a case (in which more than one edge of the bone in the joint may be identified in the reconstructed image), it is determined whether the identified edge of the bone is concave or convex. A convex edge of the bone may be then identified as a target edge of the bone in the joint. This process allows a target edge of the bone covered with cartilage to be accurately selected from multiple bones in the joint, leading to accurate measurement of the thickness or the like of the cartilage.

Since the reconstructed images, such as the absorption image, differential phase image, and small-angle scattering image, are all reconstructed from the same moire image taken by the X-ray Talbot imaging apparatus 1, the edge of the bone in the joint is at the same position in these reconstructed images. Information on the identified position of the edge of the bone (e.g., the coordinates of the corresponding pixels in the reconstructed image) may be applied to a differential phase image to identify the position of the edge of the bone in the differential phase image. Thus, the image processing apparatus 50 in Exemplary Configuration 1 is configured to identify the position of the edge of the bone in a reconstructed image and then applies the resulting information to the differential phase image to identify the position of the edge of the bone in the differential phase image.

The image processing apparatus 50 then displays the identified bone edge on a screen 51a of the display 51 as shown in FIG. 3, for example. The identified bone edge is represented with a white broken line in FIG. 3, but may be represented in any form that allows the user to visually recognize the position of the identified bone edge on the screen 51a.

Figure 4:
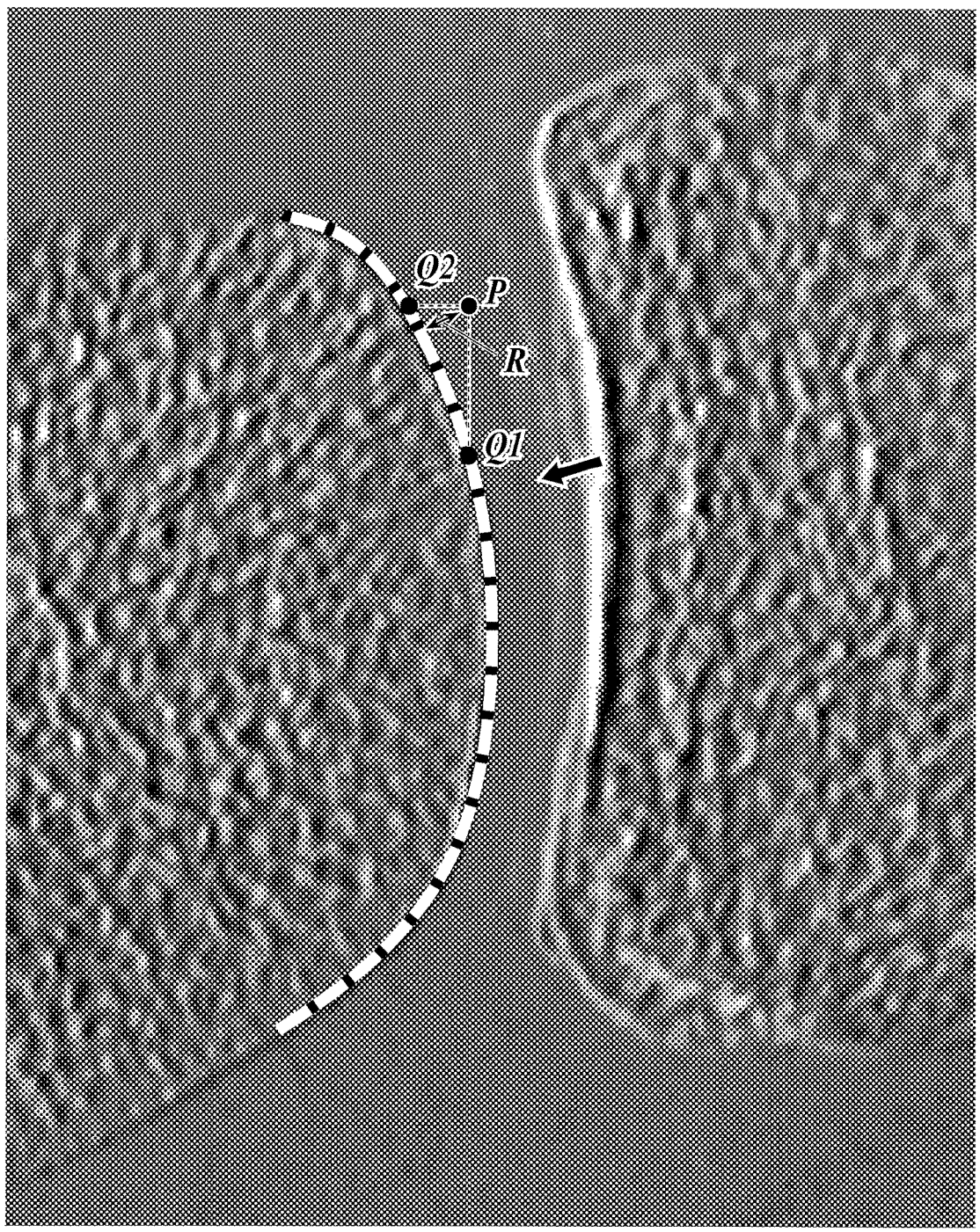
FIG. 4 is a photograph showing the edge of the cartilage in the joint identified in Exemplary Configuration 1, the specified position P on the edge of the cartilage, the thickness R of the cartilage in the position P, and other feature values.

After the user specifies the positions on the edge of the joint cartilage in the differential phase image on the display 51 (see "1", "2", and "3" in FIG. 3), the image processing apparatus 50 calculates the shortest distance from each specified position to the edge of the bone as the thickness of the joint cartilage at the specified position. In particular, as shown in FIG. 4, the image processing apparatus 50 calculates distances r from a specified position P to the positions on the edge of the joint cartilage in the differential phase image and defines the shortest distance r as the thickness R of the joint cartilage in the position P (see "cartilage thickness" in FIG. 3, for example), thus achieving quantitative measurement.

If all the positions on the identified edge of the bone in the differential phase image undergo the above distance calculating procedure, unnecessary calculation increases the time for measuring the thickness R in the position P. To avoid this, as shown in FIG. 4, the image processing apparatus 50 may determine points Q1 and Q2 on the edge of the bone, the points Q1 and Q2 being the nearest points in the vertical and horizontal directions from the position P in the differential phase image. The image processing apparatus 50 may calculate the shortest distance for a limited portion, i.e., between the points Q1 and Q2, of the edge of the bone.

In such a case, the points Q1 and Q2 should be determined on the edge of the bone covered with the target cartilage including the position P. In some cases, however, the edge of not only the bone on the left of FIG. 4 (having a convex face) but also the bone on the right of FIG. 4 (having a concave face) are detected and the points Q1 and Q2 are determined on the edge of the bone on the right of FIG. 4. To prevent such a phenomenon and to determine the exact points Q1 and Q2, the following procedure is carried out.

Figure 5:
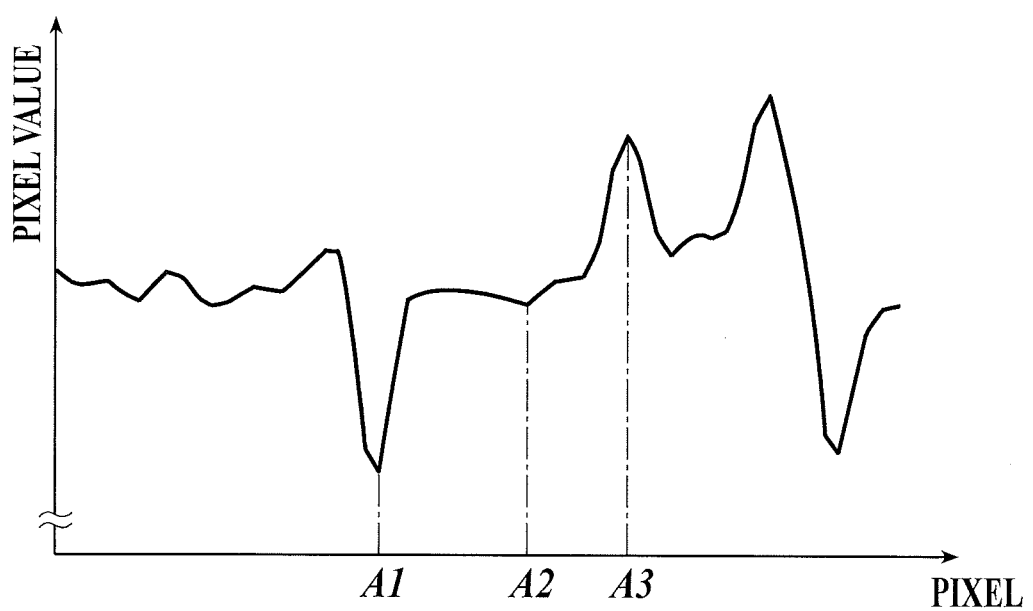
FIG. 5 is a graph of an example profile of pixel values detected by sequentially scanning a target pixel row in the differential phase image from left to right.

FIG. 5 is a graph of the values of the pixels in the pixel row including the position P in the differential phase image, as described later. The position P specified on the edge of the target cartilage has a local minimum pixel value indicated by A2 in the graph of FIG. 5. Accordingly, the edge of the bone on the left of FIG. 4 covered with the target cartilage also has a local minimum pixel value indicated by A1 in the graph. The edge of the bone on the right of FIG. 4 (uncovered with the target cartilage) has a local maximum pixel value indicated by A3 in the graph. If the right-left direction of the finger (subject) is reversed, the edges of the target cartilage and the bone covered with the target cartilage have local maximum pixel values, while the edge of the bone uncovered with the target cartilage has a local minimum pixel value.

Upon the determination of the position P, the values of the pixels in the pixel row including the position P in the differential phase image are detected (see the graph of FIG. 5). It is then determined whether the edge (position P) of the target cartilage has a local minimum or maximum pixel value. The edge having a pixel value with the same tendency as the pixel value of the position P is selected from the edge of the bone on the left of FIG. 4 (having a convex face) and the edge of the bone on the right of FIG. 4 (having a concave face). If the position P (the edge of the cartilage) has a local minimum pixel value, the bone edge having a local minimum pixel value is selected. If the position P has a local maximum pixel value, the bone edge having a local maximum pixel value is selected. This procedure allows the point Q2 (see FIG. 4) to be determined correctly.

The point Q1 can be correctly determined on the edge of the bone on the left of FIG. 4 (having a convex face), not on the edge of the bone on the right of FIG. 4 (having a concave face), in a similar manner after the detection of the values of the pixels in the pixel row including the position P in the differential phase image. Alternatively, the user may determine the points Q1 and Q2 on the edge of the bone in the joint.

The shortest distance is then calculated for the range between the determined points Q1 and Q2 on the edge of the bone, which saves the time to measure the cartilage thickness R in the position P and reduces the load on the image processing apparatus 50. There are cases in which the line extending from the position P in the vertical or horizontal direction in the differential phase image does not meet the edge of the bone in the joint, and in which the point Q1 or Q2 cannot be detected. When only one of the points Q1 and Q2 on the edge of the bone is detected, the detected point (Q1 or Q2) and the coordinates of the position P are used for the calculation. For instance, a rectangle having an edge including the position P and the detected point (Q1 or Q2) is determined in the differential phase image, and the shortest distance is calculated for the bone edge within the rectangle. If only the point Q1 is determined, a pixel row including the position P in the differential phase image may be defined as one of the upper and lower edges of the rectangle, and a pixel row including the point Q1 may be defined as the other. If only the point Q2 is determined, a pixel column including the position P in the differential phase image may be defined as one of the right and left edges of the rectangle, and a pixel column including the point Q2 may be defined as the other. The shortest distance may be calculated for only a predetermined area of the rectangle, instead of the whole area of the rectangle (which extends in the row direction if only the point Q1 is detected and the column direction if only the point Q2 is detected).

As shown in FIG. 3, in the normal mode, the thickness R of the joint cartilage is measured for multiple positions P on the edge cartilage ("1", "2", and "3" in FIG. 3). For instance, when the user specifies the first position P1 (e.g., "1" in FIG. 3) on the edge of the cartilage in the differential phase image, the image processing apparatus 50 may measure the thickness R of the cartilage for the position P1 as described above, then determine one or more pixels that are near the position P1 and have values within a predetermined range from the pixel value of the position 1, and then indicate the determined pixels on the differential phase image as candidates for the position P2 (e.g., "2" in FIG. 3). Thus, the user can just select the position P2 from the candidates. This procedure facilitates the user work in the measurement of the thickness R. Optionally, the image processing apparatus 50 may calculate the shortest distances for the candidates for the position P2 while indicating the candidates on the differential phase image, so that the thickness R for the position P2 can be displayed on the screen 51*a* upon the determination of the position P2 by the user.

[Exemplary Configuration 2]

In Exemplary Configuration 1, the position of the edge of the bone is identified in the differential phase image. The shortest distance is then calculated from the position on the identified edge of the bone to the position P on the joint cartilage edge specified by the user. The shortest distance is defined as the thickness R in the position P, achieving quantitative measurement.

In Exemplary Configuration 2, the position of the joint cartilage edge is identified in the differential phase image. The shortest distance is then calculated from the position of the identified edge of the joint cartilage to a position on the edge of the bone specified by the user. The shortest distance is defined as the thickness R at the specified position, achieving quantitative measurement.

As described in Exemplary Configuration 1, in the differential phase image of FIG. 2B, the pixel value steeply decreases at the edge portion of the bone having an articular head (see A1 in FIG. 5), then rises, then slightly decreases to a local minimum value (see A2 in FIG. 5), and then steeply rises (see A3 in FIG. 5) when every pixel value is sequentially observed pixel by pixel from left to right in the target pixel row. The point A3 corresponds to the edge of the bone having a concave face (i.e., an articular fossa), which is the on the right of FIG. 2B. The point A2 at a local minimum value between the points A1 and A3 corresponds to the edge of the joint cartilage.

In Exemplary Configuration 2, the image processing apparatus 50, for example, detects the point A2 between the detected points A1 and A3 by sequentially observing every pixel value pixel by pixel from left to right in a target pixel row in the differential phase image. The differential phase image is sequentially scanned in the vertical direction row by row for this procedure to identify the position of the edge of the joint cartilage in the differential phase image.

Figure 6:
FIG. 6 is a photograph showing the edge of the bone in the joint identified in Exemplary Configuration 2, the specified position p on the edge of the bone, the thickness R of the cartilage in the position p, and other feature values.

Unlike in Exemplary Configuration 1, after the edge of the joint cartilage is identified, a position p on the edge of the bone in the joint is specified in the differential phase image on the display 51 by the user as shown in FIG. 6, and the image processing apparatus 50 calculates the shortest distance from the position p to the edge of the joint cartilage as the thickness R of the joint cartilage in the position p. Thus, the thickness R of the joint cartilage in the position p can be measured quantitatively also in Exemplary Configuration 2.

In Exemplary Configuration 2, the thickness of the cartilage may be measured at multiple positions on the edge of the bone in the joint in the differential phase image as in Exemplary Configuration 1. As in Exemplary Configuration 1, the image processing apparatus 50 may determine the points on the edge of the cartilage, the points being the nearest points in the vertical and horizontal directions from the position p in the differential phase image. The image processing apparatus 50 may calculate the shortest distance or measure the thickness R for a limited portion, i.e., between the determined points, of the edge of the cartilage. Alternatively, the user may manually determine the edge of the joint cartilage by observing the differential phase image on the display 51 of the image processing apparatus 50.

As in the other exemplary configurations, the position p on the edge of the bone in the joint may be specified in any reconstructed image other than a differential phase image, such as an absorption image or a small-angle scattering image. If the point p is specified in a reconstructed image other than a differential phase image, the image processing apparatus 50 determines the corresponding point p in a differential phase image for the procedure described above.

[Exemplary Configuration 3]

In Exemplary Configuration 1, only the edge of the bone is identified in the differential phase image. In Exemplary Configuration 2, only the edge of the joint cartilage is identified in the differential phase image. In Exemplary Configuration 3, both the edge of the bone and the edge of the joint cartilage are identified in the differential phase image. In particular, the image processing apparatus 50 employs Exemplary Configuration 1 when the user specifies the position P on the edge of the joint cartilage in the differential phase image (see FIG. 4, for example), and Exemplary Configuration 2 when the user specifies the position p on the edge of the bone in the differential phase image (see FIG. 6, for example). This configuration allows the thickness R to be quantitatively measured in the position P or p.

In the case where the user specifies the position deviating from the edge of the joint cartilage or the bone in the differential phase image, the image processing apparatus 50 may determine the position P on the edge of the joint cartilage or the position p on the edge of the bone nearest to the specified position for the procedure in Exemplary Configuration 1 or 2 and measure the thickness R at the specified position. Thus, even if the user specifies the position out of the edge of the joint cartilage or bone in the differential phase image, the position specified by the user can be modified to a correct position on the edge of the joint cartilage or bone for the measurement of the thickness R. Consequently, the thickness R can be calculated more accurately.

[Exemplary Configuration 4]

In Exemplary Configurations 1 to 3, the shortest distance from the position P or p specified in the differential phase image by the user to the identified edge of the bone or cartilage is calculated as the thickness R in the position P or p, achieving quantitative measurement.

In Exemplary Configuration 4, the thickness R is calculated by another method based on the following mechanism associated with bones in a joint. A joint can be bent or stretched smoothly when the bones in the joint move smoothly against each other. Hence, as shown in FIGS. 2A and 2B and other drawings, the bone edge having a convex face (an articular head) and the bone edge having a concave face (an articular fossa) have an distinct arc shape in many cases. In contrast, the edges of the bones in a knee joint look straight depending on the viewing direction (or the direction of the knee joint in the differential phase image).

Accordingly, the edge of the bone in the joint in the differential phase image may be subjected to curve or straight-line fitting for quantitative measurement of the thickness R. In Exemplary Configuration 4, the image processing apparatus 50 subjects the edge of the bone to curve or straight-line fitting based on multiple dots determined on the edge of the bone in the joint in the differential phase image (see the white broken line in FIG. 4, for example) or based on multiple dots determined by the user. When the user specifies any position on the edge of the bone for the measurement of the thickness R, the thickness R can be quantitatively measured on the normal line to the straight or curve line for the specified position.

Exemplary Configuration 4 will now be described in detail. In Exemplary Configurations 4 and 5, the edge of the bone in the joint is fitted to an arc shape, but may be fitted to a straight line or an elliptic curve, instead. Arc-shape fitting requires three points on the edge of the bone to yield one arc. Straight-line fitting requires two points on the edge of the bone to yield one straight line. Elliptic-curve fitting requires five points on the edge of the bone to yield one elliptic curve. Arc fitting of the edge of the bone, for example, may include fitting the edge to an arc based on varying combinations of three points selected from at least four predetermined points on the edge of the bone. With the multiple obtained fitted arcs, the shape of the edge of the bone is fitted to an arc more accurately. Alternatively, the edge of the bone may be fitted to an arc based on multiple points on the edge of the bone in the differential phase image, using the least squares or Hough transform, for example. This applies to fitting using any line or curve other than a straight line and an arc.

Figure 7:
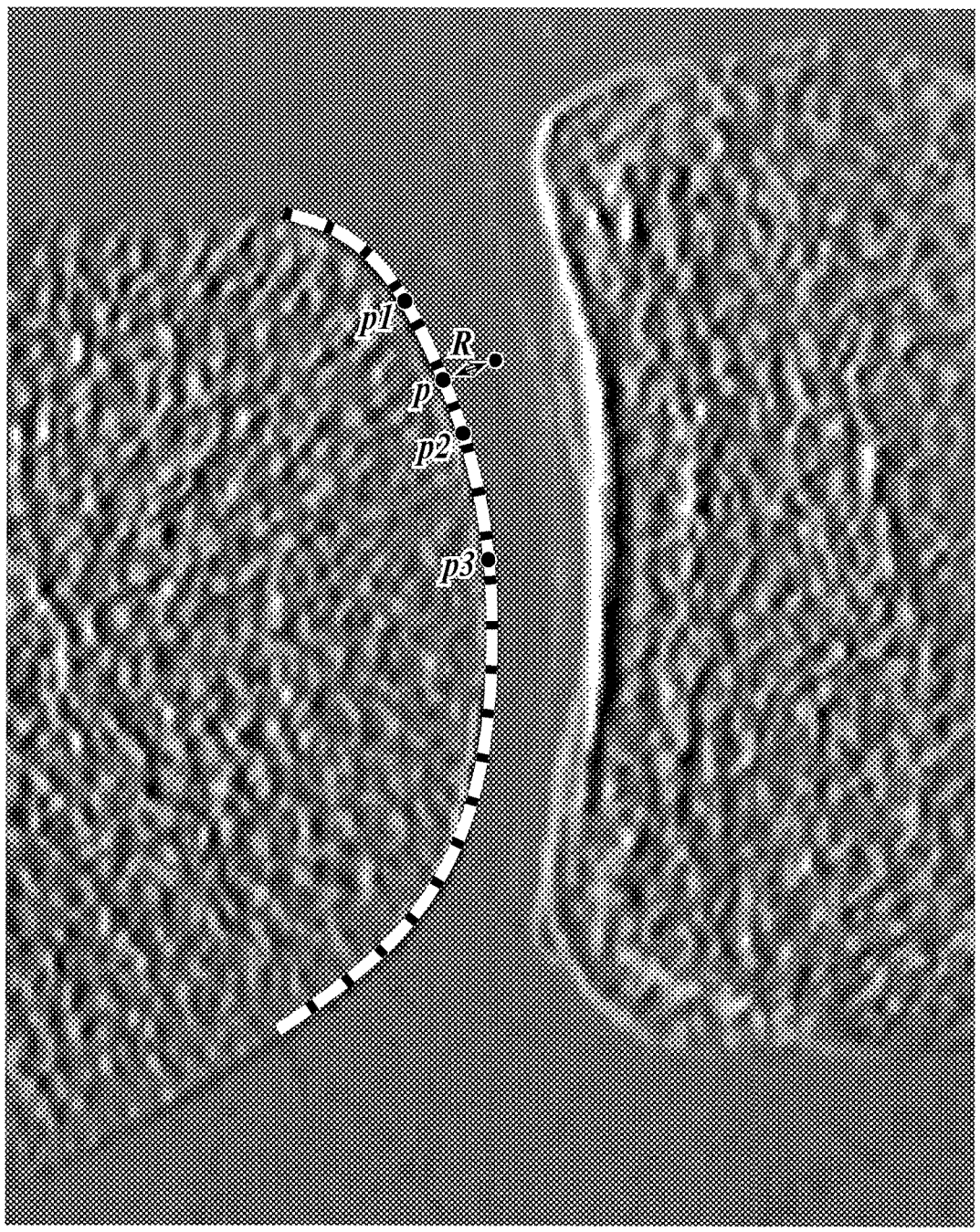
FIG. 7 is a photograph showing three points determined on the edge of the bone in the joint identified in Exemplary Configuration 4, for example.
Figure 8:
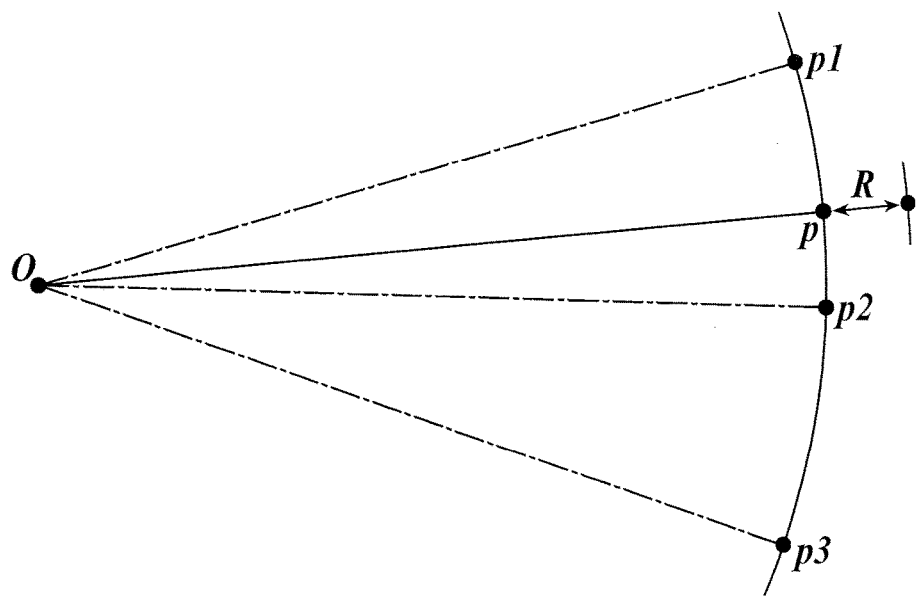
FIG. 8 illustrates an arc based on the three points, the center O of the arc, the normal line passing through the position p, and the thickness R of the cartilage, for example.

Upon the identification of the edge of the bone in the differential phase image, the image processing apparatus 50 determines three points p1, p2, and p3 on the edge of the bone as shown in FIG. 7, for example. Alternatively, the user determines three points p1, p2, and p3 on the edge of the bone. As shown in FIG. 8, then the image processing apparatus 50 determines an arc based on the three points p1, p2, and p3. As shown in FIGS. 7 and 8, upon the determination of the position p on the edge of the bone by the user, the normal line to an arc at the position p is determined. The edge of the cartilage is then detected on the normal line and the distance is measured as the thickness R in the position p, achieving quantitative measurement.

For instance, the edge of the cartilage on the normal line is detected in the following manner. The values of the pixels on the normal line are sequentially observed from the position p on the edge of the bone. The values of the pixels on the normal line are plotted as in FIG. 5, although FIG. 5 does not illustrate a profile of the values of the pixels on the normal line, but illustrates a profile of the values of the pixels on the target row in the differential phase image as described above. Hence, the edge of the joint cartilage can be detected by detecting a pixel corresponding to A2 in FIG. 5 at which the pixel value slightly decreases to a local minimum value after an increase from a much lower value in the position p. The thickness R in the position p can be measured accurately and quantitatively by calculating the distance between the position p and the position of the edge of the cartilage.

When the edge of the bone is fitted to an arc based on the determined three points: p1, p2, and p3, the normal line to the arc at the position p can be represented by a straight line passing through the center O of the arc (see FIG. 8) and the position p. Upon the determination of the position p on the edge of the bone, the image processing apparatus 50 calculates a straight line passing through the position p and the center O determined at the calculation of the arc to which the edge of the joint cartilage is fitted. The values of the pixels on the straight line (i.e., normal line) may be observed sequentially from the position p to detect the edge of the joint cartilage. This configuration facilitates accurate measurement of the thickness R in the position p.

In Exemplary Configuration 4, as in Exemplary Configuration 1, the edge of the bone may be identified in a reconstructed image other than a differential phase image, such as an absorption image or a small-angle scattering image, and the resulting information may be then applied to a differential phase image to identify the edge of the bone in the differential phase image. In addition, the user may determine multiple points on the edge of the bone in any reconstructed image other than a differential phase image, and the resulting information may be applied to a differential phase image to determine the multiple points on the edge of the bone in the differential phase image.

Alternatively, the user may determine multiple points on the edge of the bone in a differential phase image or other reconstructed images, without a process in which the image processing apparatus 50 or the user specifies the edge of the bone in the differential phase image. In such a case, the image processing apparatus 50 fits the edge of the bone to a straight or curved line based on the multiple points and determines the straight or curved line to be the edge of the bone in the differential phase image. This applies to a process in which the image processing apparatus 50 fits the edge of the joint cartilage to a straight or curved line based on the multiple points in Exemplary Configuration 5 described below.

[Exemplary Configuration 5]

In Exemplary Configuration 5, multiple points are determined on the edge of the joint cartilage identified in the differential phase image instead of the edge of the bone identified in the differential phase image in Exemplary Configuration 4. In particular, the image processing apparatus 50 or the user determines multiple points on the edge of the joint cartilage in the differential phase image. The image processing apparatus 50 then fits the edge of the cartilage to a straight or curved line based on the multiple points, and then quantitatively measures the thickness R on the normal line to the straight or curved line at the position P on the edge of the joint cartilage.

Exemplary Configuration 5 is similar to Exemplary Configuration 4, and thus its detailed description will be omitted. In Exemplary Configuration 4, the edge of the cartilage is detected by sequentially observing the values of the pixels on the normal line outward from the position p on the edge of the bone (i.e., outward from the center O if the edge of the bone is fitted to an arc). In Exemplary Configuration 5, the edge of the bone is detected by sequentially observing the values of the pixels on the normal line inward from the position P on the edge of the joint cartilage (i.e., toward the center O if the edge of the cartilage is fitted to an arc).

In Exemplary Configuration 4, the edge of the bone may be identified in any reconstructed image other than a differential phase image, such as an absorption image or a small-angle scattering image, and the resulting information may be applied to a differential phase image so that the edge of the bone can be identified in the differential phase image. In Exemplary Configuration 5, the edge of the joint cartilage is identified in a differential phase image or a reconstructed image generated from a differential phase image, since the edge of joint cartilage appears only in differential phase images or images generated from differential phase images as described above.

In Exemplary Configurations 4 and 5, the edge of the bone or cartilage in the image may be fitted to a parabola, a hyperbola, or other curves, in addition to a straight line, a circle (arc), and an ellipse.

[Exemplary Configuration 6]

In Exemplary Configurations 4 and 5, the edge of the bone in a reconstructed image (including a differential phase image) or the edge of the joint cartilage in a differential phase image is fitted to an arc. In Exemplary Configuration 6, the polar coordinate system is applied to a differential phase image or a reconstructed image (including a differential phase image) to quantitatively measure the thickness R from the resulting image.

Figure 9:
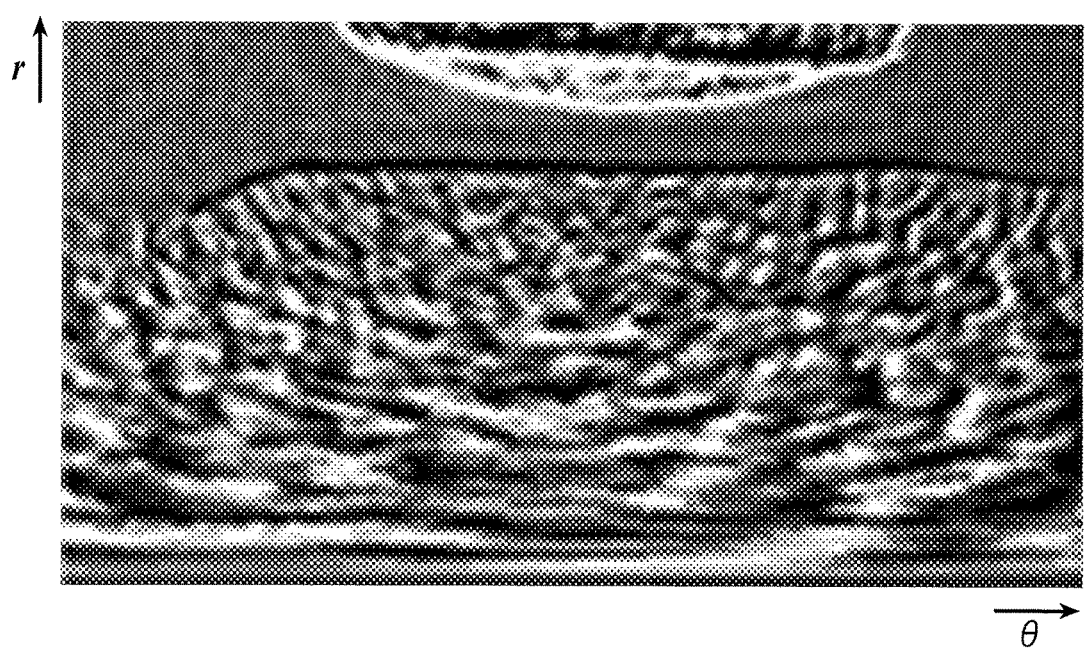
FIG. 9 is an image (photograph) obtained by applying polar coordinates to the differential phase image of the joint in FIG. 2B.

In Exemplary Configurations 1 to 5 (see FIGS. 3 to 8), a differential phase image or other images is expressed in Cartesian coordinates in which pixels are each represented by coordinates (i,j), where i is the pixel row number and j is the pixel column number. In Exemplary Configuration 6, the Cartesian coordinates are converted to polar coordinates expressing each pixel by (θ,r), where θ is an angle about the center O of an arc and r is the distance from the center O. The center O is calculated from the arc to which the edge of the bone or cartilage is fitted based on at least three points of p1, p2, and p3 on the edge of the bone (see FIG. 8) or cartilage in the differential phase image. Thus, the thickness R is measured quantitatively. FIG. 9 is an image obtained by converting the differential phase image of the joint in FIG. 2B to the expression in polar coordinates. The joint in FIG. 9 is rotated by 90° from that in FIG. 2B.

Referring to FIG. 9, which is an image expressed in polar coordinates, the edge of the bone having a convex face (specifically, a portion of the edge which is well fitted to an arc) in the Cartesian coordinate system (i.e., in FIG. 2B) is represented by a substantially straight line. The edge of the cartilage is also represented by a substantially straight line parallel to it (FIG. 9 shows the cartilage of a healthy subject not having a disease such as arthrorheumatism.

The normal line to the arc at the position P or p in Exemplary Configurations 4 and 5 is represented by a straight line extending along the r axis (the vertical axis in FIG. 9) in the image of FIG. 9 expressed in polar coordinates. The image processing apparatus 50 observes a profile (like FIG. 5) of pixel values along a straight line parallel to the r axis and passing through the position P on the edge of the joint cartilage or the position p on the edge of the bone in such an image expressed in polar coordinates, and calculates the distance between the points A1 and A2 in the profile (see FIG. 5) to quantitatively measure the thickness R in the position P or p. This configuration allows the thickness R to be measured readily and accurately. The straight light parallel to the r axis corresponding to the normal line can advantageously be shifted in the θ axis direction (horizontally in FIG. 9) continuously or at regular angles for scanning to measure the thickness R at each angle θ readily and accurately.

It should be understood that Exemplary Configurations 1 to 5 can also perform measurement while shifting the position P or p on the edge of the cartilage or bone continuously or at regular intervals. Such a configuration enables accurate measurement of the thickness R at each position. Exemplary Configuration 1 or 2 may be applied to the image of FIG. 9 expressed in polar coordinates to quantitatively measure the distance from the position P on the cartilage edge to the nearest point on the bone edge or the distance from the position p on the bone edge to the nearest point on the cartilage edge and determine the distance to be the thickness R in the position P or p.

Advantageous Effect 1

As described in Exemplary Configurations 1 to 6, in the medical imaging system 100 of this embodiment including the X-ray Talbot imaging apparatus 1 and the image processing apparatus 50, the image processing apparatus 50 can quantitatively measure the thickness R of cartilage in a joint by reference to the edge of the bone or cartilage in the joint identified in a differential phase image (or an image generated from a differential phase image) generated by the controller 19 in the X-ray Talbot imaging apparatus 1. Thus, unlike in traditional techniques, the thickness R can be quantitatively measured by the image processing apparatus 50 automatically, independently of the experience or techniques of a radiologist, achieving consistent measurement of the thickness R.

[Calculation of Feature Value of Thickness of Cartilage]

In the above description, the thickness R of cartilage in a joint in the specified position P or p is quantitatively measured. Alternatively, the thicknesses R in multiple positions P or multiple positions p may be measured and a feature value of each thickness R, such as a maximum value, a minimum value, an average value, a difference between the maximum value or average value and the minimum value, and a ratio of the minimum value to the maximum value or average value, may be calculated.

Alternatively, the difference between the typical cartilage thickness and the measured thickness R or the ratio of the typical cartilage thickness to the measured thickness R at a specified position of a target joint (e.g. the third joint (MP joint) of a forefinger, the second joint (PIP joint) of a middle finger, or a knee joint) may be determined to be a thickness feature. In this case, values or models of typical cartilage thickness dependent on the age, gender, and the type of joint may be predetermined from samples of healthy subjects. Among them, an appropriate value or model of typical cartilage is selected depending on patient's age and gender and the type of the target joint. Also measured is the thickness Ranother of cartilage in another joint of the patient not having a disease (not deformed by a disease) near the target joint of the patient for calculation of a thickness feature value. The original thickness R* of cartilage in the target joint before deformation may be estimated from the thickness Ranother and used as the typical thickness.

In the case where the positions P or p are continuously shifted on the edge of the cartilage or bone for the measurement of the thickness R as described above, the feature values of each thickness R may be measured within a portion of the edge of the cartilage or bone in which the position P or p is continuously shifted.

In case of a defect or other deformation of joint cartilage (see D in FIG. 10), this configuration allows the level of such a defect or other deformation to be quantitatively and accurately estimated as a feature value. This configuration can also estimate a change in the shape of the cartilage quantitatively and accurately, for example, from a difference between the current and prior feature values, i.e., a time-dependent change in feature value. A doctor, for example, can accurately recognize the progression of the abrasion or other damage in patient's cartilage over time, by reference to a time-dependent change in thickness feature (see FIGS. 11A and 11B, for example).

[Estimation of Shape of Cartilage Edge Before Deformation]

In the calculation of a feature value of the thickness of the cartilage, the original thickness R* (before deformation) of the cartilage in patient's diseased joint may be estimated as described above. The thickness R* or shape of the cartilage before deformation is estimated from the thickness Ranother, which is the thickness of another joint that is not deformed by a disease as stated above, or may be estimated in any of the following manners.

[Estimation Process 1]

The image processing apparatus 50 estimates the shape of the joint cartilage before deformation by reference to the edge of the bone in a differential phase image. In particular, the edge of the bone is identified in the differential phase image as in Exemplary Configuration 1 (see FIGS. 3 and 4, for example), for example. As shown in FIGS. 7 and 8, at least three points are determined on the identified edge of the bone. The edge of the bone is then fitted to an arc based on the at least three points to specify the position of the center O of the arc (see FIG. 8). The distance between the center O and each position on the edge of the bone is enlarged by an appropriate factor to estimate the shape of the cartilage before deformation.

The enlargement factor of the distance between the center O and each position on the edge of the bone may be determined, for example, depending on a maximum value of the thickness R measured in the above manner. In specific, the distance between the center O and each position on the edge of the bone may be enlarged by the same factor such that the edge of the bone after the enlargement matches the position of the edge of the cartilage at which position the cartilage thickness R has a maximum value (i.e. a position on the normal line passing through the position.

In the joint before deformation, the shape of the bone edge and the shape of the cartilage edge have substantially similar figure about the center O in many cases. Accordingly, for a joint in which the shape of the bone edge and the shape of the cartilage edge have substantially similar figure, the shape of the bone edge after the enlargement of the distance between the center O and each position on the edge of the bone is estimated as the shape of the cartilage edge before deformation. Thus, the cartilage edge before deformation can be estimated exactly.

In the above description, the shape of the bone edge obtained by enlarging the distance between the center O and each position on the edge of the bone based on a maximum value of the measured thickness R is estimated as the shape of the cartilage edge before deformation. Alternatively, the shape of the bone edge enlarged based on the value or model of typical thickness of cartilage in the joint may be estimated as the shape of the cartilage edge before deformation, in which case also the cartilage edge before deformation can be estimated efficiently.

[Estimation Process 2]

In the above description, the shape of the identified bone edge is directly enlarged and estimated as the shape of the cartilage edge before deformation. In Estimation process 2, the identified bone edge is fitted to an arc. The arc is then enlarged and estimated as the shape of the cartilage edge before deformation. In this case, too, the radius of the arc, i.e., the distance r from the center O may be enlarged based on a maximum value of the measured thickness R or based on the value or model of typical thickness of cartilage in the joint, and the enlarged arc may be estimated as the shape of the cartilage edge before deformation.

As described in Exemplary Configuration 6, the differential phase image may be expressed in polar coordinates indicated by the angle $\theta$ to the center O of the arc, to which the bone edge is fitted, and the distance r from the center O (see FIG. 9), and the bone edge expressed in polar coordinates may be translated in the direction of the increasing distance r (i.e. upward in FIG. 9) and estimated as the shape of the cartilage in the joint before deformation expressed in polar coordinates. In addition, the edge of the bone in the joint in polar coordinates may be fitted to a straight line, and the straight line may be translated in the direction of the increasing distance r (i.e. upward in FIG. 9) and estimated as the shape of the cartilage edge before deformation expressed in polar coordinates.

[Estimation Process 3]

Figure 10:
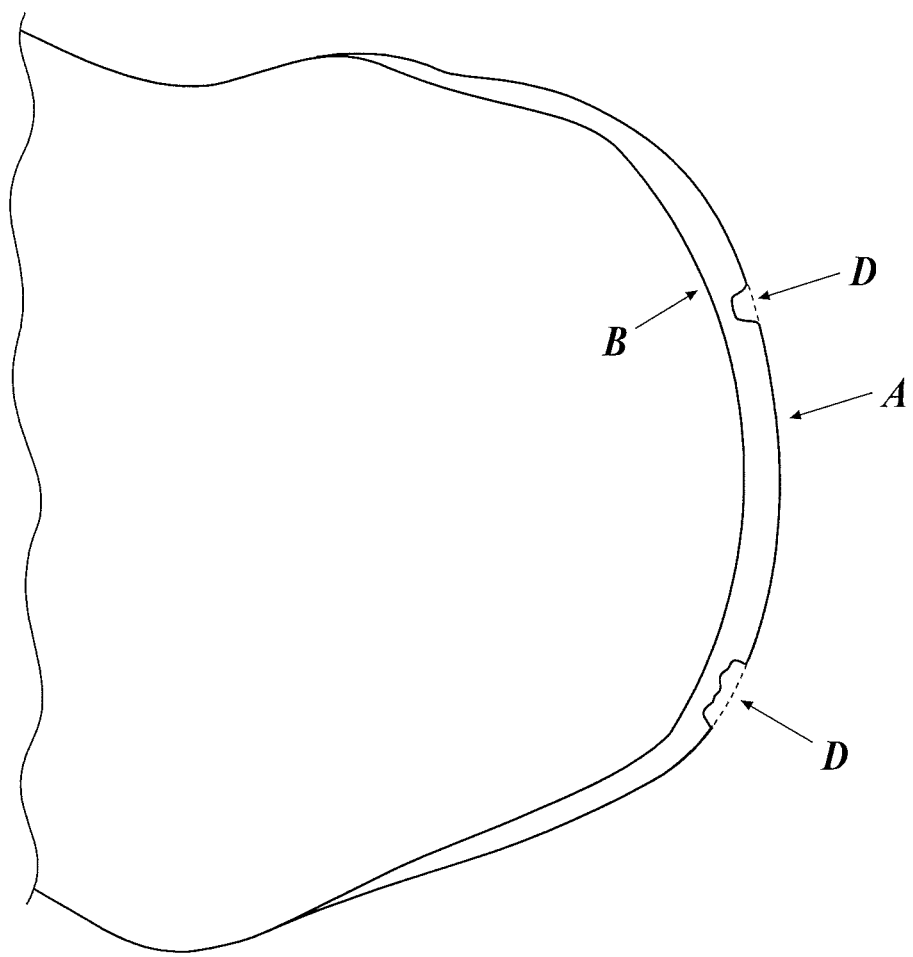
FIG. 10 illustrates defects in cartilage and estimates the shape of the cartilage before deformation by restoring the cartilage having the defects to its original state.

As shown in FIG. 10, the identified cartilage has defects D at its edge A in the differential phase image in some cases. A bone edge B is also illustrated in the drawing. In such cases, the shape of the cartilage before deformation (see the dashed line in FIG. 10), i.e., without the defects D can be estimated, for example, from a convex curve determined based on the shape of a portion of the cartilage edge having no defect. Also in Estimation processes 2 and 3, the shape of the cartilage edge before deformation can be efficiently estimated.

[Presentation of Estimated Shape of Cartilage Edge Before Deformation]

Figure 11A:
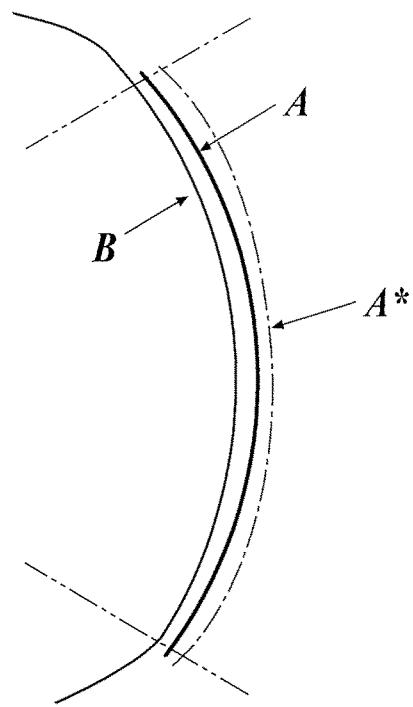
FIG. 11A illustrates the estimated shape of the edge of the cartilage before deformation, superimposed on a differential phase image.
Figure 11B:
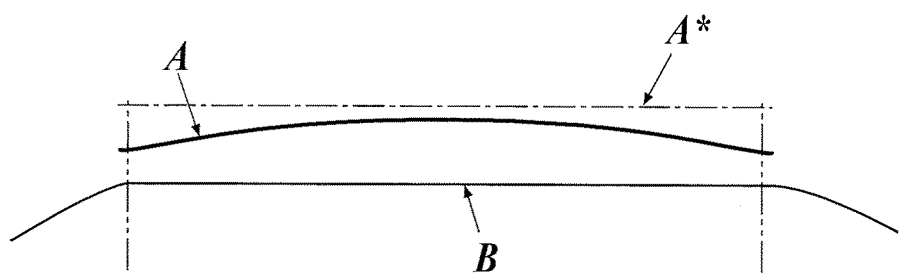
FIG. 11B illustrates the estimated shape of the edge of the cartilage before deformation, superimposed on a differential phase image in polar coordinates.

The image processing apparatus 50 can superimpose the shape of the cartilage edge before deformation estimated in any of Estimation processes 1 to 3, on a differential phase image (see FIG. 11A) or differential phase image in polar coordinates (see FIG. 11B) of the cartilage and display the resulting image. FIGS. 11A and 11B illustrate a cartilage edge A and bone edge B identified in a differential phase image and a differential phase image expressed in polar coordinates. The alternate long and short dashed line A* indicates the estimated shape of the cartilage edge before deformation.

Thus, a doctor, for example, can compare the shape of the cartilage edge A on the screen of the image processing apparatus 50 with the estimated shape of the cartilage edge A* before deformation and visually recognize the level of deformation, e.g., defect or abrasion of the cartilage readily and accurately for diagnosis.

[Calculation of Feature Value of Shape of Cartilage]

In addition, a feature value of the shape of the cartilage which indicates the level of abrasion or other deformation of the cartilage may be calculated by reference to the shape of the cartilage edge A* before deformation estimated in the differential phase image and the shape of the cartilage edge A identified in the image (see FIG. 11A), or the shape of the cartilage edge A* before deformation estimated in the differential phase image expressed in polar coordinates and the shape of the cartilage edge A identified in the image (see FIG. 11B).

Like the feature values of the cartilage thickness R, the feature values of the shape of the cartilage may include a maximum value, a minimum value, an average value, a difference between a maximum value or average value and a minimum value, and a ratio of a minimum value to a maximum value or average value of a ratio of the thickness R of the actual cartilage to the thickness of the shape of the cartilage A* before deformation within the region defined by the chain double-dashed lines in the drawings or within a predetermined portion of the region.

The feature values of the shape of the cartilage may also include the area of the cartilage (i.e., the area of a region between the cartilage edge A and the bone edge B) and the area of a portion of the cartilage lost by the deformation (i.e., the area of a portion between the cartilage edge A and the estimated cartilage edge A* before deformation) in a region defined by the chain double-dashed lines in the drawings or within a predetermined portion of the region, and a ratio of the area of the cartilage or the area of a portion of the cartilage lost by the deformation to the area of the cartilage before deformation (i.e., the area of a portion between the bone edge B and the estimated cartilage edge A* before deformation).

In case of a defect or other deformation of the joint cartilage (see D in FIG. 10, for example), this configuration allows the level of defect or other deformation to be quantitatively and accurately measured as a feature value of the shape of the cartilage. This configuration can also estimate a change in the shape of the cartilage quantitatively and accurately, for example, from a difference between the current and prior feature values, i.e., a time-dependent change in feature value. A doctor, for example, can accurately determine the progression of the abrasion or other damage in patient's cartilage over time, by reference to a time-dependent change in feature value (see FIGS. 11A and 11B, for example)

Advantageous Effect 2

As described in Estimation processes 1 to 3, in the medical imaging system 100 of this embodiment including the X-ray Talbot imaging apparatus 1 and the image processing apparatus 50, the image processing apparatus 50 may estimate the shape of the cartilage before deformation by reference to the edge of the bone or cartilage identified in a differential phase image or a differential phase image expressed in polar coordinates and display an image. For example, a doctor, can compare the edge of the cartilage with the superimposed estimated shape of the cartilage edge before deformation in the displayed image and visually recognize the level of deformation of joint cartilage readily for accurate diagnosis.

Alternatively, the estimated shape of the cartilage edge before deformation may be used to calculate a feature value of the shape of the cartilage. Thus, a doctor, for example, can quantitatively and accurately recognize the level of defect or other deformation as a feature value of the shape of the cartilage, and accurately determine the progression of the abrasion or other damage in patient's cartilage over time.

It should be appreciated that the present invention should not be limited to the above embodiments and may be modified as appropriate without departing from the scope of the present invention.

The entire disclosure of Japanese Patent Application No. 2013-246853 filed on Nov. 29, 2013 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A medical imaging system comprising:
    an X-ray Talbot imaging apparatus comprising:
        an X-ray source which emits X-rays,
        an X-ray detector including conversion elements to generate an electrical signal according to the emitted X-rays, and reading the electrical signal generated by the conversion elements, as an image signal,
        a subject table to hold a subject for a joint of the subject to be imaged, and
        a controller which generates a reconstructed image from the image signal of the imaged subject, the reconstructed image including at least a differential phase image; and an image processing apparatus which measures a thickness of cartilage in the joint in the differential phase image or an image generated from the differential phase image, by reference to at least one of i) an edge of a bone in the joint identified in the reconstructed image or an image generated from the reconstructed image and ii) an edge of the cartilage identified in the differential phase image or the image generated from the differential phase image.

2. The medical imaging system according to claim 1, wherein the image processing apparatus calculates a shortest distance from a position specified on the edge of the cartilage in the differential phase image or the image generated from the differential phase image to the identified edge of the bone, and defines the shortest distance as the thickness of the cartilage at the specified position.

3. The medical imaging system according to claim 2, wherein the image processing apparatus determines points on the edge of the bone and calculates the shortest distance from the specified position on the edge of the cartilage to a portion, between the determined points, of the edge of the bone, wherein the determined points are nearest points in vertical and horizontal directions from the specified position in the differential phase image or the image generated from the differential phase image.

4. The medical imaging system according to claim 1, wherein the image processing apparatus calculates a shortest distance from a position specified on the edge of the bone in the reconstructed image or the image generated from the reconstructed image to the identified edge of the cartilage, and defines the shortest distance as the thickness of the cartilage at the specified position.

5. The medical imaging system according to claim 4, wherein the image processing apparatus determines points on the edge of the cartilage and calculates the shortest distance from the specified position on the edge of the bone to a portion, between the determined points, of the edge of the cartilage, wherein the determined points are nearest points in vertical and horizontal directions from the specified position in the reconstructed image or the image generated from the reconstructed image.

6. The medical imaging system according to claim 1, wherein the image processing apparatus fits the identified edge of the cartilage or bone to a straight or curved line based on a plurality of points determined on the edge of the cartilage or bone, and measures the thickness of the cartilage on a normal line to the straight or curved line at a position specified on the edge of the cartilage or bone.

7. The medical imaging system according to claim 6, wherein the image processing apparatus fits the edge of the cartilage or bone to an arc based on at least three points determined on the edge of the cartilage or bone, determines a center of the arc, and measures the thickness of the cartilage on a straight line passing through the specified position on the edge of the cartilage or bone and the center of the arc.

8. The medical imaging system according to claim 7, wherein the image processing apparatus fits the edge of the bone to the arc based on the at least three points determined on the edge of the bone, generates another arc obtained by enlarging a radius of the arc to which the edge of the bone is fitted, and estimates the another arc to be a shape of the cartilage before deformation.

9. The medical imaging system according to claim 8, wherein the image processing apparatus displays an image of the estimated shape of the cartilage before deformation superimposed on the differential phase image of the cartilage or the image generated from the differential phase image.

10. The medical imaging system according to claim 8, wherein the image processing apparatus determines a feature value of the shape of the cartilage by reference to i) the shape of the cartilage before deformation estimated using the differential phase image or the image generated from the differential phase image and ii) the shape of the identified edge of the cartilage.

11. The medical imaging system according to claim 6, wherein the image processing apparatus detects the edge of the bone or cartilage by reference to a profile of values of pixels on the normal line to the straight or curved line at the specified position on the edge of the cartilage or bone in the differential phase image or the image generated from the differential phase image, and measures the distance from the specified position to the detected edge of the bone or cartilage as the thickness of the cartilage at the specified position.

12. The medical imaging system according to claim 1, wherein the image processing apparatus expresses the differential phase image or the image generated from the differential phase image in polar coordinates indicated by an angle to a center of an arc and by a distance from the center, and measures the thickness of the cartilage in the image expressed in polar coordinates, the arc being an arc to which the edge of the cartilage or bone is fitted.

13. The medical imaging system according to claim 12, wherein the image processing apparatus translates the edge of the bone expressed in polar coordinates and estimates the translated edge of the bone to be a shape of the cartilage before deformation expressed in polar coordinates.

14. The medical imaging system according to claim 13, wherein the image processing apparatus displays an image of the estimated shape of the cartilage before deformation superimposed on the differential phase image expressed in polar coordinates or the image generated from the differential phase image expressed in polar coordinates.

15. The medical imaging system according to claim 13, wherein the image processing apparatus determines a feature value of the shape of the cartilage by reference to i) the shape of the cartilage before deformation estimated using the differential phase image expressed in polar coordinates or the image generated from the differential phase image expressed in polar coordinates and ii) the shape of the identified edge of the cartilage.

* * * * *